United States Patent [19]
Peters

[11] Patent Number: 5,645,603
[45] Date of Patent: Jul. 8, 1997

[54] METHOD OF ENHANCING PHYSICAL PROPERTIES OF NON-ELASTOMERIC THERMOPLASTIC MATERIALS AND RESULTING COMPOSITIONS

[76] Inventor: William E. Peters, 1026 Richwood Dr., Danville, Ind. 46122

[21] Appl. No.: 505,522

[22] Filed: Jul. 25, 1995

[51] Int. Cl.⁶ ............................ A61F 2/30; C08K 3/30; C08K 3/10; C08L 23/02
[52] U.S. Cl. .......................... 623/20; 623/18; 623/22; 523/113; 523/115; 524/406
[58] Field of Search ................ 524/406; 523/113, 523/115; 623/18, 20, 22

[56] References Cited

U.S. PATENT DOCUMENTS

| | | | |
|---|---|---|---|
| 2,710,290 | 6/1955 | Safford et al. | 260/41 |
| 2,719,833 | 10/1955 | Vincent et al. | 260/33.6 |
| 2,951,721 | 9/1960 | Asp | 288/16 |
| 3,019,206 | 1/1962 | Robb | 260/29.6 |
| 3,230,919 | 1/1966 | Crawford | 114/67 |
| 3,575,123 | 4/1971 | Shepherd et al. | 114/67 R |
| 3,878,031 | 4/1975 | Dormer | 428/365 |
| 3,940,554 | 2/1976 | Kaufman | 260/888 |
| 4,075,158 | 2/1978 | Coale | 260/42.17 |
| 4,096,207 | 6/1978 | Saxon et al. | 260/900 |
| 4,129,550 | 12/1978 | Nametkin et al. | 260/42.22 |
| 4,183,887 | 1/1980 | Karg | 264/130 |
| 4,215,178 | 7/1980 | Martin, Jr. | 428/421 |
| 4,326,046 | 4/1982 | Miyaka et al. | 525/276 |
| 4,385,019 | 5/1983 | Bernstein et al. | 264/49 |
| 4,387,168 | 6/1983 | Morita | 521/54 |
| 4,477,630 | 10/1984 | Saito et al. | 525/133 |
| 4,507,439 | 3/1985 | Stewart | 525/199 |
| 4,520,170 | 5/1985 | Kitto | 525/200 |
| 4,596,839 | 6/1986 | Peters | 523/175 |
| 4,735,982 | 4/1988 | Orndorff | 524/269 |
| 4,767,818 | 8/1988 | Boutni | 524/505 |
| 4,962,136 | 10/1990 | Peters | 523/220 |
| 5,418,270 | 5/1995 | Peters | 524/406 |

FOREIGN PATENT DOCUMENTS

| | | | |
|---|---|---|---|
| 005748 | 3/1975 | Japan . | |
| 032655 | 2/1983 | Japan | 524/406 |
| 076566 | 5/1985 | Japan . | |
| 60-199045 | 8/1985 | Japan . | |
| 110558 | 4/1989 | Japan | 524/406 |
| 996764 | 6/1965 | United Kingdom . | |

OTHER PUBLICATIONS

Chemical Abstract 99:106291.
Shell Chemical Company publication SC:198–92, *Kraton Polymers for Adhesives and Sealants*.
Shell Chemical Company publication SC:68–92 *Kraton Thermoplastic Rubber*.
Amax, Inc. article, *How Does MoS₂ Differ From Other Solid Lubricants?*
Imperial Chemical Industries, Ltd. reprint of Kirk–Othmer Encyclopedia of Chemical Technology, vol. 9, 2nd Ed., 1966, pp. 805–831 *'FLUON': Polytetrafluoroethylene*.
ICI Americas, Inc. product information brochure, *Fluon CD 1*.
ICI Americas, Inc. product information brochure, *Fluon CD 525*.
Dow Corning Corp. product description, *Information About MOLYKOTE Specialty Lubricants*, 1979.
Amax, Inc. product data sheet SC–9, *Molybdenum Products*, 1985.

*Primary Examiner*—David Buttner
*Attorney, Agent, or Firm*—Brinks Hofer Gilson & Lione

[57] ABSTRACT

A modified non-elastomeric thermoplastic composition includes a non-elastomeric thermoplastic modified by molybdenum disulfide, polytetrafluoroethylene and an elastomeric binder.

12 Claims, No Drawings

METHOD OF ENHANCING PHYSICAL PROPERTIES OF NON-ELASTOMERIC THERMOPLASTIC MATERIALS AND RESULTING COMPOSITIONS

The present invention relates to modified non-elastomeric thermoplastic materials and particularly to non-elastomeric thermoplastic plastics modified by modifiers that include molybdenum disulfide, polytetrafluoroethylene, and an elastomeric binder, preferably an elastomeric block copolymer.

BACKGROUND OF THE INVENTION

Non-elastomeric thermoplastic materials have been developed for use in a wide variety of applications. Non-elastomeric thermoplastic materials include many high polymers, usually synthetic, that are substantially solid, with little or no cold flow and plasticity, and can be formed or molded under heat and pressure and, sometimes, machined to high dimensional accuracy. Such non-elastomeric thermoplastic materials include those frequently referred to by the term "plastics" including, for example, polystyrene, polyurethane, polyethylene, polypropylene, acrylonitrile-butadiene-styrene, polyvinyl chloride, nylons, cellulosic resins, acrylic resins and the like. However, the mechanical properties of each individual non-elastomeric thermoplastic material, frequently limits the applications appropriate to that thermoplastic material. For instance, polyethylene is a generally inexpensive and non-elastomeric material with generally acceptable mechanical properties at very low temperatures and reasonable heat resistance. However, polyethylene has a low melting point and is not generally satisfactory for use in high temperature applications. Polystyrene is a generally non-elastomeric thermoplastic material that is generally not resistant to outdoor weathering, but has good optical qualities and has chemical resistance to most household acids. Other non-elastomeric thermoplastic materials generally have some advantageous properties, but also have disadvantageous properties, and many non-elastomeric thermoplastic materials have low resistance to impact, particularly at low temperatures.

Compositions, called modifiers, have been added to non-elastomeric thermoplastic materials to modify or enhance the mechanical properties such as abrasion resistance, solvent resistance, useful life, strength, and the like. Conventional modifiers typically include ethylene-propylene rubber (EPR), ethylene-propylene diene monomer (EPDM), nitrile-butadiene rubber (NBR), natural rubber (NR), ethylene-vinyl acetate copolymer (EVA), thermoplastic polyolefin rubber (TPO), as well as various other elastomers.

In the past, such modifiers have achieved only limited success, particularly in improving flame retardancy, hot and cold flow, chemical inertness, impact resistance, and resistance to ozone ($O_3$) and ultraviolet light (UV). In addition, such conventional modifiers are typically blended with the thermoplastic in relatively high concentrations, that is, more than 10 percent by volume. These high concentrations of modifier increase the cost of the modified thermoplastic material and, therefore, a finished product. Moreover, even with the use of high concentrations of such modifiers, manufacturers of the modified thermoplastic compounds are limited to less than 5 percent fillers and extenders, such as reground tires, which can reduce the cost of the finished product.

The present invention provides improved non-elastomeric thermoplastic materials of the type generally referred to with the term "Plastics". Where, in this application, I refer to "non-elastomeric thermoplastic materials", or "non-elastomeric thermoplastics", I mean high polymer plastics, usually synthetic, that are substantially solid, with minimal plasticity and cold flow at normal atmospheric temperatures, and can be formed or molded with heat and pressure and, in some high polymer plastics, machined to high dimensional accuracy, including such high polymer plastics as polystyrene, polyurethane, polypropylene, polyethylene, acrylonitrile-butadiene-styrene, polyvinyl chloride, nylons, cellulose resins, acrylic resins and the like. Such improved non-elastomeric thermoplastics are modified with a modifier comprising an elastomer composition, polytetrafluoroethylene (PTFE), and molybdenum disulfide ($MoS_2$), and can provide greatly improved physical properties, such as impact resistance, flame retardancy, flow characteristics, chemical inertness, and improved weatherability (such as resistance to $O_3$ and UV), and can achieve such improvements at lower percentages of modifier, while permitting the non-elastomeric thermoplastic material to be loaded with increased percentages of fillers and extenders.

BRIEF STATEMENT OF THE INVENTION

U.S. Pat. No. 5,418,270, the disclosure of which is incorporated herein by reference, discloses a modified thermoplastic elastomeric composition comprising PTFE, $MoS_2$ and an elastomeric block copolymer. Thermoplastic elastomeric block copolymers differ in molecular structure from typical plastic and commercial rubbers, which are generally homopolymers or random copolymers. That is, thermoplastic elastomeric block copolymers generally comprise two incompatible polymers, a thermoplastic end block polymer, typically polystyrene, chemically joined with one of several elastomeric mid block polymers. In use, the block copolymers tend to provide an elastic lattice structure interconnected by domains formed by their thermoplastic end blocks. Since the lattice structure is the result of physical rather than chemical forces, it may be destroyed either by dissolving the copolymer in a solvent or by heating it beyond the glass transition temperature of its thermoplastic end blocks. Upon evaporation of the solvent or cooling below the glass transition temperature of its thermoplastic end blocks, a structure may be re-imparted to the block copolymer. Such block copolymers are thus recyclable.

Thermoplastic block copolymers can include styrene-butadiene-styrene copolymers (SBS), styrene-isoprene-styrene copolymers (SIS) and styrene-ethylene/butylene-styrene copolymers (SEBS). In addition to the traditional ABA-type tri-block polymers, such copolymers are available in the radial $(A-B)_n$ and a di-block (A-B) structures. Prior to processing, the polystyrene end blocks of such copolymers are associated in rigid domains through physical cross-linking to yield a continuous three dimensional network. During processing in the presence of heat and shear or solvent, the polystyrene domains soften and permit flow and after cooling, then reform to lock the interconnecting elastomeric network in place. The styrene domains can impart high tensile strength to the resulting structure and the elastomeric mid block polymers can impart elasticity, cold flow flexibility and fatigue resistance.

The thermoplastic elastomeric compositions disclosed in the '270 patent are useful in modifying the properties of asphalt, as disclosed in U.S. Pat. No. 5,393,819.

The present invention provides improved non-elastomeric thermoplastics with substantially improved physical properties, particularly increased impact resistance and flame retardancy. In the present invention, a modifier, comprising fibrillated PTFE, $MoS_2$ and a non-vulcanized elastomeric material is blended with a non-elastomeric thermoplastic to improve physical properties of the non-elastomeric thermoplastic material.

In preferred embodiments of the invention, the modifier portion of the non-elastomeric thermoplastic material comprises a fibrillatable PTFE, which has been preassociated with $MoS_2$, combined with a thermoplastic elastomeric material, preferably an elastomeric block copolymer, in relative amounts, for example, from as low as about 1.5 parts per hundred rubber (pphr) to as high as about 10 pphr of thermoplastic elastomeric copolymer. The modifier portion can further include an unpolymerized PTFE residue of the fibrillated PTFE. In the invention such a modifier is blended with a non-elastomeric thermoplastic in the range of about 1.5 percent to about 10 percent modifier, with the balance of non-elastomeric thermoplastic and fillers.

The invention includes a method for making a modified non-elastomeric thermoplastic composition. The method includes the steps of forming a modifier including $MoS_2$ and fibrillatable PTFE and a non-vulcanized elastomeric material, pelletizing the modifier, blending the pelletized modifier with pelletized non-elastomeric thermoplastic material, and pelletizing the blended modifier and non-elastomeric thermoplastic material to form a modified non-elastomeric thermoplastic composition.

According to one aspect of the invention, the pelletized modified non-elastomeric thermoplastic composition can be loaded with fillers, such as reground tires by blending the modified non-elastomeric thermoplastic material and fillers and extruding them with an extrusion temperature elevated about 10° F. above the temperature recommended by the thermoplastic material manufacturer.

In preferred methods of the invention, the forming step includes the steps of preassociating the $MoS_2$ and fibrillatable PTFE and combining the preassociated $MoS_2$ and fibrillatable PTFE with a quantity of thermoplastic elastomeric copolymer in a high shear mixer that provides sufficient shear to fibrillate the polytetrafluoroethylene. The blending step includes the step of combining the pelletized modifier and the pelletized non-elastomeric thermoplastic in a high shear mixer that provides sufficient shear to thoroughly blend the modifier and non-elastomeric thermoplastic to form the modified non-elastomeric thermoplastic composition. After blending, the modified non-elastomeric thermoplastic composition is pelletized.

Whenever composition ingredients are expressed in percentages, it is to be understood that the expressed percentage is the percent by weight of the resulting composition, unless otherwise stated. Where compositions are expressed in parts, it is to be understood that they are expressed in parts per hundred rubber by weight.

DETAILED DESCRIPTION OF A PREFERRED EMBODIMENT

The present invention provides improved non-elastomeric thermoplastic materials including non-elastomeric thermoplastics such as polystyrene, polyurethane prepolymer, polypropylene, acrylonitrile-butadiene-styrene, polyvinyl chloride, nylons, cellulosic resin and acrylic resin. The improved non-elastomeric thermoplastics can be used in diverse applications and products, such as electrical insulators, aircraft canopies, gears, plumbing fixtures, football helmets, battery cases, toys, telephones, fabric coating, bearing surfaces, squeeze bottles, packaging films, trash containers, auto parts and construction materials.

In the invention, non-elastomeric thermoplastics are modified by the addition of a non-vulcanite elastomeric binder, i.e., a thermoplastic elastomeric copolymer, combined with fibrillatable PTFE, $MoS_2$ to greatly enhance mechanical properties of the non-elastomeric thermoplastic.

The thermoplastic elastomeric copolymers used in the modifiers preferably comprise thermoplastic elastomeric block copolymers. The elastomeric block copolymers generally comprise at least two incompatible polymers that react to form a two-phase copolymer including thermoplastic polymer end blocks and an elastomeric polymer mid block. In use, the thermoplastic polymer end blocks form, as one phase, discrete thermoplastic "domains" that are separate from interconnecting elastomeric "chains", as the second phase, formed by the elastomeric mid block polymers. Thermoplastic elastomeric copolymers that may be used include the thermoplastic elastomers sold by the Shell Chemical Company of Houston, Tex., as their KRATON D-grades and KRATON G-grades, the thermoplastic elastomers sold by EniChem Elastomeri Srl of Milano, Italy, and EniChem Elastomers Ltd. of South Hampton, Great Britain as their EUROPRENE products, and synthetic thermoplastics sold by Firestone Synthetic Rubber and Latex Company of Akron, Ohio, under the brand name of Stereon. These thermoplastic non-vulcanite elastomers include linear styrene-butadiene-styrene copolymers, branch styrene-butadiene copolymers, linear styrene-isoprene-styrene copolymers, branch styrene isoprene copolymers, linear styrene-ethylene/butylene-styrene copolymers, and di-block styrene ethylene-propylene copolymers.

Compositions of the invention can also combine non-elastomeric thermoplastic materials, and fibrillatable PTFE and $MoS_2$ with conventional modifiers such as non-vulcanized ethylene-propylene rubber (EPR), ethylene-propylene diene monomer (EPDM), nitrile-butadiene rubber (NBR), natural rubber (NR), ethylene-vinyl acetate copolymer (EVA), thermoplastic polyolefin rubber (TPO), as well as various elastomers. Adding $MoS_2$ and fibrillatable PTFE to conventional modifiers and non-elastomeric thermoplastics according to the present invention dramatically improves the effect of the conventional modifiers on the physical properties of the non-elastomeric thermoplastics. (See Example 1).

The elastomeric binder portion of the modifiers used in the invention can also include polyester, polyurethane and polyamide block copolymers, and polypropylene/ethylene-propylene copolymers, and some compatible monomers, polymers and terpolymers.

In the modifiers used in non-elastomeric thermoplastic materials of the invention, such thermoplastic binders are combined with fibrillatable PTFE particles and $MoS_2$ particles, which are preferably preassociated. The fibrillatable PTFE preferred for use in the invention is a coagulated dispersion polymer such as FLUON CD1 made by ICI Americas, DF11X made by Ausimont, or TEFLON K-10 made by E. I. duPont de Nemours. FLUON CD1 is a preferred fibrillatable PTFE in the invention because it can be dispersed more readily in the elastomer and fibrillates with a greater length-to-diameter ratio than other fibrillatable PTFE.

In the past, such coagulated dispersions have been exposed at high temperatures in drying the particulate resin material. The fibrillatable PTFE preferably used in my invention should be exposed to lower temperatures in drying the particulate resin material to obtain fibrillatable PTFE particles capable of fibrillation to achieve very high lengthto-diameter ratios. In addition, such fibrillatable PTFE is accompanied by an unpolymerized PTFE residue. Preferred coagulated dispersions can be extruded through a small orifice (e.g., orifice with a cross section of about ¼ inch or less) by a hydraulic ram with pressures of only about 12,000 psi, while non-preferred resins require markedly higher ram pressures of, for example, 15,000 psi.

As indicated above, it is believed that the manner in which the coagulated dispersion polymers that comprise fibrillatable PTFE are processed during their manufacture affects the structure of the fibrillatable PTFE particles and the ease with which they may be fibrillated into fibers having a high ratio of fiber length to fiber diameter. Although it is not clearly understood, it is further believed that altering manufacturing processes to reduce dense or hard layers on the outside of the PTFE polymer particles permits the particles to be drawn into longer and thinner fibers. Among the factors used in manufacturing coagulated dispersions that may increase the surface hardness of the coagulated dispersion PTFE particles are the processing steps used to avoid further agglomeration of the coagulated dispersion PTFE particles and to remove anti-agglomeration agents and water from, and dry, the coagulated dispersion particles. Use of high temperatures, for example, to remove lubricants and water and dry the coagulated dispersion particles may tend to make the surface of coagulated dispersion particles harder or more dense and render them more difficult to fibrillate.

The preferred $MoS_2$ is technical grade powder such as that sold by Amax, Inc. as its technical grade. Such powdered $MoS_2$ generally has, in technical grade, about 85 percent of its particles smaller than 44 microns and may be provided with small average particle sizes (e.g., less than ten microns), and is characterized by substantial purity with over 98 percent comprising $MoS_2$ and less than 2 percent comprising such materials as insoluble acids, minerals, carbon, water and oil. Molybdenum disulfide withstands pressures exceeding 500,000 psi and is serviceable through temperatures of $-375°$ F. to $750°$ F.

The $MoS_2$ particles are an important part of this invention. Fibrillatable PTFE alone tends to sheet rather than fibrillate when an attempt is made to mix it with thermoplastic elastomeric copolymer. It is believed that the $MoS_2$ permits more intimate engagement of the fibrillated PTFE and thermoplastic elastomeric copolymer structure through its reaction with the surfaces of the PTFE and thermoplastic elastomeric copolymer.

In manufacturing the modifier used in this invention, the particles of fibrillatable PTFE and $MoS_2$ are preferably preassociated. In preparing the preassociated combination of PTFE and $MoS_2$, particulate fibrillatable PTFE and particulate $MoS_2$ are preferably placed together in a mixing apparatus, such as a rotating mixing barrel, and intermixed together. Preferably, the particle size of the $MoS_2$ particles is generally many times smaller than the particle size of the fibrillatable PTFE. Fibrillatable PTFE can have median particle sizes as large as 450 to 600 microns, although average particle sizes substantially smaller than 450 to 600 microns can be used. The $MoS_2$ used in the invention is preferably technical grade and has a substantial majority of particles with sizes less than about 45 microns, with average particle sizes as small as about four microns and less. The average particle size of the $MoS_2$ can be one-twentieth that of the fibrillatable PTFE and smaller. The particulate matter is mixed together for a sufficient time that the $MoS_2$ particles are generally adherent to the fibrillated PTFE particles, and the mixture particles become uniformly grey-black in appearance. As an example, 150 pounds of additive material was obtained with 15 minutes of agitation and mixing.

The adherence of the $MoS_2$ particles to the particulate PTFE is due to an electrostatic charge differential between the PTFE particles and the MoS particles. The electrostatic charge differential is developed by rolling the PTFE in a mixing barrel to impart to a negative charge to the PTFE. Preferably, the mixing barrel is made of polypropylene, or similar material, and includes wooden paddles for agitating the PTFE in the barrel. After the PTFE has been rolled, $MoS_2$ is added to the PTFE and the mixture is rolled. The natural diamagnetic positive charge of the $MoS_2$ combines with the negative charge imparted to the PTFE to provide the electrostatic charge differential.

The prior association of $MoS_2$ particles with fibrillatable PTFE particles greatly assists the fibrillation and uniform combination of the fibrillated PTFE with the thermoplastic elastomer copolymer in this invention. The $MoS_2$ particles associated with the surface of the fibrillatable PTFE particles, it is believed, enhance the combination of the fibrillated PTFE particles with the elastomeric polymer phase of the thermoplastic copolymer and deter an adherent association of the PTFE particles with themselves. Furthermore, it is believed that the coating of $MoS_2$ particles on the fibrillatable PTFE particles interacts with the surrounding thermoplastic elastomeric copolymer upon mixing and assists in the fibrillation of the PTFE.

One component of the modifier used in the invention comprises fibrillatable PTFE, preferably FLUON CD1from ICI Americas, Inc., which is soft as a result of lower temperature drying of the PTFE particles during manufacture and capable of extrusion through a small orifice by a hydraulic ram at pressures of 12,500 psi plus or minus 500 psi, and a technical grade $MoS_2$ powder, such as that sold by Amax, Inc., and Cyprus Industrial Minerals Company, generally adherent to the fibrillatable PTFE particles. The ratio of fibrillatable PTFE to $MoS_2$ in the additive is preferably from about 3 to 1 to about 6 to 1 by weight. The preassociated PTFE and $MoS_2$ combine more easily with some thermoplastic elastomeric copolymers than with others, and it may be possible and advisable to produce the preassociated PTFE and $MoS_2$ components with ratios other than as set forth above.

In the manufacture of a modifier used in the invention, the thermoplastic elastomeric copolymer, preferably in crumb-like or powder-like form and, preferably, the preassociated fibrillatable PTFE and the $MoS_2$ particles are combined in a high shear mixer such as, preferably, a twin screw extruder or any other mixing and/or extruding apparatus which may provide sufficient shear to fibrillate the fibrillatable PTFE particles, for example, a Banbury mixer. The thermoplastic elastomeric copolymer, PTFE and $MoS_2$ are mixed under high shear until the mixture becomes uniform in appearance.

In addition, while it is preferred to combine a preassociation of fibrillatable PTFE and MoS particles with pellet-like thermoplastic elastomeric copolymer, the copolymer can be combined with the fibrillatable PTFE and MoS particles separately. In such a situation, after placing the thermoplastic elastomeric copolymer in the shear-producing mixing and/or extruding apparatus, fibrillatable PTFE particles and $MoS_2$ particles are then added to the apparatus as mixing is effected. The amount of $MoS_2$ used in the invention to effect a more uniform and effective combination of the fibrillated PTFE and the thermoplastic elastomeric copolymer may be easily determined by adding the $MoS_2$ to the fibrillatable PTFE-copolymer mixture until the fibrillatable PTFE becomes uniformly fibrillated and mixed with the copolymer.

In preferred methods of manufacturing the modifier used in the present invention, about 93 percent of the fibrillatable PTFE particles are converted to fibrils, that is, elongated, solid PTFE fiber-like elements, with shear. As noted above, fibrillatable PTFE is a coagulated dispersion, and may include as much as 10 percent (by weight) of non-solid "binder" which is not converted into fibrils. This binder is unpolymerized PTFE. It is theorized that the unpolymerized PTFE acts like a chemically inert coating for the thermoplastic copolymer structure, and the fibrillated PTFE mechanically combines with the elastomeric mid block polymers, that is, the elastomeric polymer portion of the molecular structure formed by the lattice of thermoplastic elastomeric copolymer. It is also theorized that it is the unpolymerized PTFE binder that provides fluoridation of the modified non-elastomeric thermoplastic compositions of the invention to enhance their flame retardancy.

One example of a modifier used in the invention comprises 100 parts rubber of EniChem linear SBS copolymer SOL T6302 combined with two parts (per hundred rubber) of preassociated fibrillatable PTFE and molybdenum disulfide particles sold by Alphaflex Industries, Inc. under their tradename Alphaflex 101. Alphaflex 101 includes a preassociation of FLUON CD1 fibrillatable PTFE particles having diameters in the range of about 100 to about 600 microns, and $MoS_2$ particles having an average particle size in the range of about one to about ten microns being largely adherent to the fibrillatable PTFE particles. The modifier results from mixing the linear SBS T6302 copolymer and Alphaflex 101 additive together in a twin screw extruder until substantially all of the fibrillatable PTFE is fibrillated and uniformly mixed with the linear SBS T6302 copolymer and extruded as a modifier for use in the invention. Preferably, the modifier is pelletized during the extrusion process.

In preferred methods of combining the modifier with a non-elastomeric thermoplastic, the pelletized modifier is mechanically blended with pelletized non-elastomeric thermoplastic, and the intermixed pellets are extruded to form a modified non-elastomeric thermoplastic composition of the invention. The pelletized modifier and non-elastomeric thermoplastic are combined in a production extruder. The modified non-elastomeric thermoplastic composition can be pelletized during the extrusion process.

The use of the elastomeric composition disclosed in the '270 patent to provide an improved modifier for non-elastomeric thermoplastics have, until now, been unsuccessful. Attempts to blend the elastomeric composition of the '270 patent with thermoplastics have resulted in separate agglomerations of thermoplastic material, elastomeric composition, and, when included, reground tires. The materials would not blend together properly under conventional conditions. It is important to note that, during the extrusion of the modified non-elastomeric thermoplastic composition of the invention, the final stage temperature of the extruder should be raised about 10° F. above the normally recommended temperature. The temperature increase improves the viscosities of the modifier and the non-elastomeric thermoplastic components and permits more thorough blending of those components by the extruder. Without the temperature increase, the modifier and thermoplastic may not blend together acceptably, but, rather, exit the extruder as an unmixed, lumpy agglomeration of the components. Of course, for any particular modified non-elastomeric thermoplastic, a greater or lesser temperature change may be required.

The present invention has a dramatic effect on the properties of non-elastomeric thermoplastics. Modified non-elastomeric thermoplastic compositions of the invention exhibit increased chemical inertness, better weatherability and ozone resistance, improved cold temperature toughness, greater impact resistance and increased flame retardancy. In one example, the flame retardancy of a modified non-elastomeric thermoplastic composition of the invention improved from a UL V-2 rating to a UL V-0 rating. In another example, high density polyethylene (HDPE) modified with a modifier comprising PTFE, $MoS_2$ and an elastomeric block copolymer is inert, with improved wear characteristics, permanent plastic deformation and no cold flow, which make it well suited for use in human joint replacement parts such as hips and knees.

The present invention adds a non-amorphous material to an amorphous material, thereby enhancing the flame retardancy and dimensional stability, as well as other physical properties of the non-amorphous material. For example, the effect of the present invention on flame retardancy of non-elastomeric thermoplastics can be especially important. Recent tests have achieved a UL V-0 flame retardancy rating, whereas previous efforts had only achieved a UL V-2 rating. The improved flame retardancy, and an improved resistance to melting and dripping, can be especially important in the consumer electronics industry. For example, when a circuit board inside a TV or computer overheats or ignites, conventional thermoplastic components or cases can melt and drip, essentially feeding the flames. Components or cases made from non-elastomeric thermoplastics modified according to the present invention, on the other hand, demonstrate a dramatic resistance to melting and dripping, thereby providing an additional measure of protection.

Another improvement to non-elastomeric thermoplastics, resulting from the fibril network formed by the modifier, includes an increased ability to accommodate fillers and extenders, such as reground tires or recycled plastic. For example, injection molded specimens of unmodified linear low density polyethylene are only able to accommodate less than 5 percent fillers. Linear low density polyethylene specimens modified according to the present invention were able to accommodate up to 40 percent reground tire. Samples containing 20 percent reground tires have been tested and showed increased impact resistance and increased rigidity as compared to unmodified compositions. The increased ability to accommodate reground tires (or other fillers) directly affects the cost of the final product by reducing the cost of materials.

Modified injection moldable polypropylene compositions of the invention have also demonstrated significantly improved flame retardancy. It is believed that the unpolymerized portion of the PTFE, which is mostly fluorine, encapsulates and coats the plastic domains of the elastomeric block copolymer of the modifier prior to the melt flow of the plastic domain. It is also believed that the fluorine in the unpolymerized portion of the PTFE is also responsible for the improved chemical inertness imparted to the modified compositions of the invention.

The invention is illustrated by the following examples:

EXAMPLE 1

A conventional modifier of SBS rubber was added to a sample of virgin polypropylene in a composition comprising 7 percent modifier and the balance polypropylene. A similar composition was formed using the invention, where the fibrillated PTFE and $MoS_2$ were added to the same SBS rubber used in the conventional modifier. The physical properties of both modified compositions were measured and compared to the physical properties of unmodified polypropylene. The comparison results, indicated below, show that both modifiers slightly reduce the flexural modulus and the flexural strength. However, the modifier of the invention dramatically improved the notched IZOD impact test value over the improvement by the conventional modifier.

| Physical Properties | Natural Polypropylene | Conventionally Modified (7%) Polypropylene | Invention Modified (7%) Polypropylene |
|---|---|---|---|
| Flexural Modulus, psi | 83,000 | 77,000 | 77,000 |
| Flexural Strength, psi | 6,400 | 5,700 | 5,700 |
| Flexural Izod ft. lb./in. | 0.09 | 0.32 | 3.5 |

EXAMPLE 2

A high impact polystyrene (HIPS) was combined in a composition of the invention comprising 7 percent modifier, including fibrillated PTFE, $MoS_2$ and 840A Stereon with 2.25 pphr PTFE, 0.75 pphr $MoS_2$, and the balance HIPS. The physical properties of the modified HIPS composition were measured and compared to manufacturer-specified values for the unmodified HIPS material. The notched izod test value for the invention modifier was almost twice that for the natural HIPS.

| Physical Properties | Natural HIP | Invention Modified (7%) HIP |
|---|---|---|
| Flexural Modulus, psi | 166,000 | 167,000 |
| Flexural Strength, psi | 6,400 | 6,000 |
| Notched Izod, ft. lb./in. | 2.7 | 4.3 |

In addition to the foregoing test results, initial testing has indicated similar results using recycled HIPS material. Thus, an additional cost savings may be realized by using recycled material.

EXAMPLE 3

An acrylic was combined in a composition of the invention comprising 5 percent modifier, including fibrillatable PTFE, $MoS_2$ and 840 A Stereon with 2.25 pphr PTFE, 0.75 pphr $MoS_2$, and the balance acrylic. The measured physical properties of the resulting composition of the invention were compared with the properties of conventionally-modified acrylic. Acrylic composition of the invention exhibited a four fold increase in impact strength over a conventionally modified sample.

| | Conventionally Modified Acrylic | Invention Modified Acrylic |
|---|---|---|
| RESIN: | | |
| Melt Flow g/10 min. | 4.2 | 3.4 |
| Density, g/cc | 1.12 | 1.17 |
| MECHANICAL: | | |
| Tensile Strength, p.s.i. | 8,200 | 9,100 |
| Flexural Modulus, p.s.i. | 390,000 | 225,000 |
| Notched Izod Impact, ft. lb./in. | 1.1 | 4.3 |

EXAMPLE 4

A linear low density polyethylene was combined in a composition of the invention comprising 5 percent modifier, including 2.25 pphr fibrillatable PTFE, 0.75 pphr $MoS_2$ and the balance 840A Stereon, with the following test results. It should be noted that the unmodified test sample was unable to accommodate as a filler 5 percent reground tires, whereas the test sample with the modifier of the present invention included as a filler 20 percent reground tires. In separate tests, the modified composition of the invention allowed an accommodation of 40 percent reground tires as filler. This dramatic improvement in accommodation of reground tires can provide a substantial cost advantage as well as a positive environmental impact.

| | LLDP | Invention Modified LLDP |
|---|---|---|
| RESIN: | | |
| Melt Flow, g/10 min. | 2.6 | 2.9 |
| Density, g/cc | 0.936 | 0.951 |
| MECHANICAL: | | |
| Notched Izod Impact, ft. lb./in. | 0.8 | 4.7 |
| Tensile @ Yield, psi | MD 1300 | 1,700 |
| | TO 1000 | 1,400 |
| Tensile @ Break, psi | MD 5100 | 5,400 |
| | TO 2500 | 2,900 |
| Elongation @ Break, % | MD 130 | 170 |
| Flexural Modulus psi | 56,000 | 142,000 |
| Reground Tires | less than 5% | 20% |

The preceding examples demonstrate that the modified non-elastomeric thermoplastic composition of the present invention exhibit enhanced physical properties. Moreover, the enhanced properties can be achieved while permitting increased loading of reground tires as filler into non-elastomeric thermoplastics. Thus, the invention provides an enhanced thermoplastic composition with a considerable cost saving advantage.

It should also be noted that compositions of the invention frequently have higher melt flows, but compositions of the invention can be molded at higher temperatures to achieve comparable production rates. In many cases, satisfactory molding of compositions of the invention can be achieved by increasing the molding temperatures only 10°–15° F. over the manufacturer's recommended molding temperature for the unmodified plastic.

Although the present invention has been described in detail with reference to a certain preferred embodiment, variations and modifications exist within the scope and spirit of the invention as described and defined in the following claims.

I claim:

1. A human joint replacement formed from a composition comprising non-elastomeric thermoplastic including a modifier comprising fibrillated PTFE, molybdenum disulfide and an elastomeric block copolymer.

2. The human joint replacement of claim 1 in the form of a hip joint part.

3. The human joint replacement of claim 1 in the form of a knee joint part.

4. The human joint replacement of claim 1 wherein the non-elastomeric thermoplastic comprises high density polyethylene.

5. The human joint replacement of claim 1 wherein the non-elastomeric thermoplastic is selected from the group consisting of high density polyethylene, polypropylene, and nylon.

6. A method of fluoridating thermoplastic materials by using polytetrafluoroethylene, the method comprising the steps of:

preassociating polytetrafluoroethylene and molybdenum disulfide;

blending the preassociated polytetrafluoroethylene and molybdenum disulfide with an elastomeric block copolymer to form a modifier; and blending the modifier with the thermoplastic.

7. The method of claim 6 wherein the preassociating step includes the step of rolling the polytetrafluoroethylene and molybdenum disulfide together in a mixing barrel.

8. The method of claim 7 wherein the mixing barrel includes a thermoplastic sidewall and wooden paddles for mixing the polytetrafluoroethylene and molybdenum disulfide together.

9. The method of claim 6 wherein the blending steps include blending in a high shear mixer.

10. The method of claim 6 the step of blending the modifier with a thermoplastic material includes the step of blending in a high shear mixer and raising the temperature about 10° F. above the temperature recommended by the manufacturer of the thermoplastic.

11. A method for improving the flame retardancy of a thermoplastic composition, the method comprising the steps of:

providing a quantity of thermoplastic;

adding a quantity of polytetrafluoroethylene preassociated with an effective amount of molybdenum disulfide and blending the polytetrafluoroethylene and molybdenum disulfide with an elastomeric block copolymer in a high shear mixer to form a modifier, and adding said modifier to said thermoplastic.

12. The method of 11 further including blending the modifier and thermoplastic in a high shear mixer to form a modified composition and extruding the modified composition at a temperature elevated about 10° F. above a recommended temperature.

* * * * *